(12) United States Patent
Grisenti et al.

(10) Patent No.: US 8,778,636 B2
(45) Date of Patent: Jul. 15, 2014

(54) CHEMO-ENZYMATIC APPROACH TO THE SYNTHESIS OF PIMECROLIMUS

(75) Inventors: Paride Grisenti, Milan (IT); Shahrzad Reza Elahi, Milan (IT); Elisa Verza, Corbetta (IT)

(73) Assignee: Euticals S.p.A., Milan (IT)

( * ) Notice: Subject to any disclaimer, the term of this patent is extended or adjusted under 35 U.S.C. 154(b) by 357 days.

(21) Appl. No.: 13/261,036

(22) PCT Filed: May 19, 2010

(86) PCT No.: PCT/IB2010/052218
§ 371 (c)(1),
(2), (4) Date: Nov. 21, 2011

(87) PCT Pub. No.: WO2010/134027
PCT Pub. Date: Nov. 25, 2010

(65) Prior Publication Data
US 2012/0064575 A1    Mar. 15, 2012

(30) Foreign Application Priority Data

May 22, 2009 (IT) .............................. MI2009A0908

(51) Int. Cl.
*C12P 19/26* (2006.01)
*C07H 7/06* (2006.01)

(52) U.S. Cl.
USPC .......................................... 435/84; 536/29.2

(58) Field of Classification Search
USPC .......................................... 435/84; 536/29.2
See application file for complete search history.

(56) References Cited

FOREIGN PATENT DOCUMENTS

| EP | 0427680 | 5/1991 |
|---|---|---|
| WO | WO 2005 105811 | 11/2005 |
| WO | WO 2006/024582 | 3/2006 |
| WO | WO 2006/040111 | 4/2006 |
| WO | WO 2006/060614 | 6/2006 |
| WO | WO 2007 103348 | 9/2007 |

OTHER PUBLICATIONS

Ferraboschi et al. Tetrahedron Lett. (available online May 25, 2009) 50: 4384-4388.*
International Search Report for PCT/1132010/052218 of Aug. 5, 2010.
IPRP for PCT/1132010/052218 of Dec. 21, 2010.
Italian Search Report for IT MI20090908 of Nov. 12, 2009.
Baumann, et al., Tetrahedron, 2003, 59, 10075-10087.
Ferraboschi, et al., Biocatalysis and Biotransformation, 2006, 24. 209-213.
Ferraboschi, et al., Biocatalysis, 1994, 10, 279-288.
Heldt-Hansen, et al., ACS Symposium Series—Biocatalysis in Argricultural Biotechnology. 1989, vol. 389, Chapter 11, 158-172.
Regen, et al., J. Org. Chem., 40, 1975, 1669-1670.
Santaniello, et al., Chem. Rev., 1992, 92, 1071-1140.
Wang, et al., J. Org. Chem., 1988, 3127-3129.

* cited by examiner

*Primary Examiner* — Susan Hanley
(74) *Attorney, Agent, or Firm* — Hueschen and Sage

(57) ABSTRACT

Processes for preparing pimecrolimus starting from ascomycin, exploiting the selectivity characteristics of the purified enzymatic systems particularly regarding the selective functionalization of the hydroxyl groups present in position 24 and 33 of ascomycin. Such method represents the first example of chemoenzymatic synthesis for preparing pimecrolimus.

35 Claims, No Drawings

CHEMO-ENZYMATIC APPROACH TO THE SYNTHESIS OF PIMECROLIMUS

The present invention regards a chemoenzymatic synthesis method for preparing pimecrolimus.

Pimecrolimus (registry number 137071-32-0; FIG. 1) is a macrolide having anti-inflammatory, antiproliferative and immunosuppressive properties. This substance is present as an active ingredient in the Elidel® drug recently approved in Europe and in the USA for topical treatment of inflammatory conditions of the skin such as atopic dermatitis.

FIG. 1: structural formula of pimecrolimus

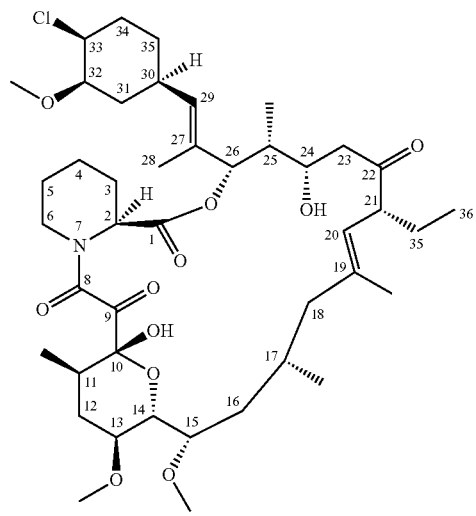

STATE OF THE ART

The preparation of pimecrolimus was described for the first time in the patent application EP427680 on behalf of Sandoz. Used as raw material in such document is ascomycin (compound identified by registry number 11011-38-4), a natural product obtained through fermentation from Streptomyces strains (such as for example *Streptomyces hygroscopicus* var *ascomyceticus*, or *Streptomyces hygroscopicus tsukubaensis* N°9993). Pimecrolimus is obtained from the ascomycin through a sequence of four steps of synthesis (scheme 1)

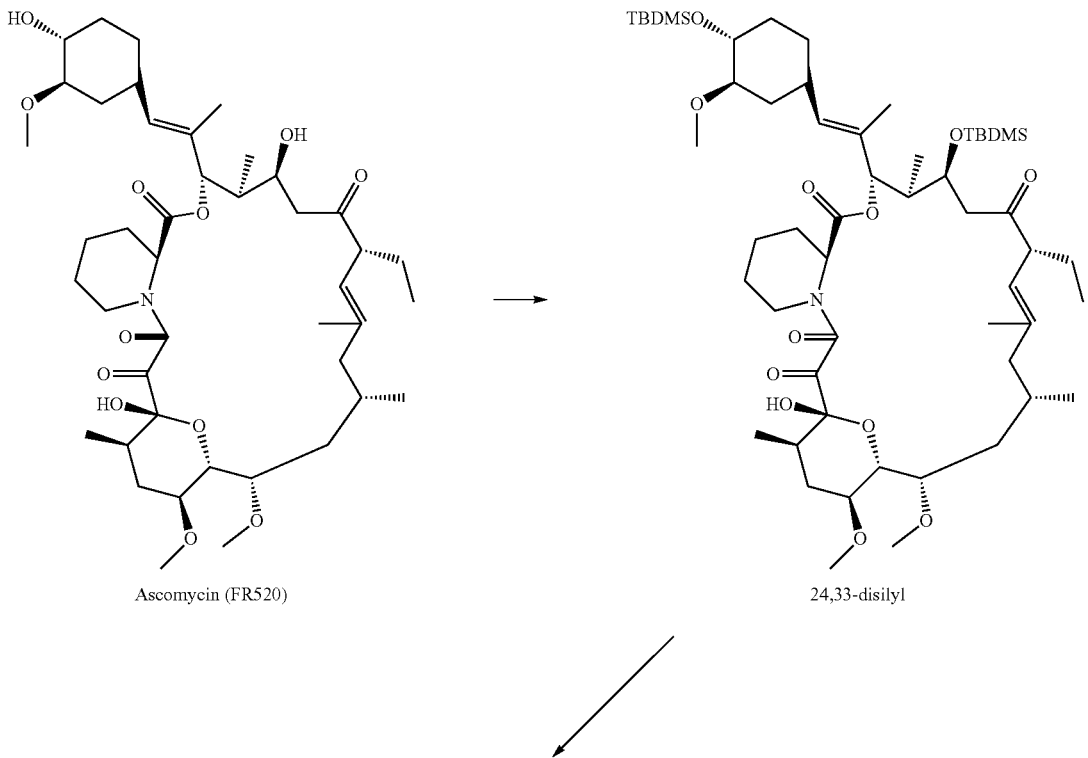

Scheme 1: synthesis process described in EP427680

Ascomycin (FR520)      24,33-disilyl

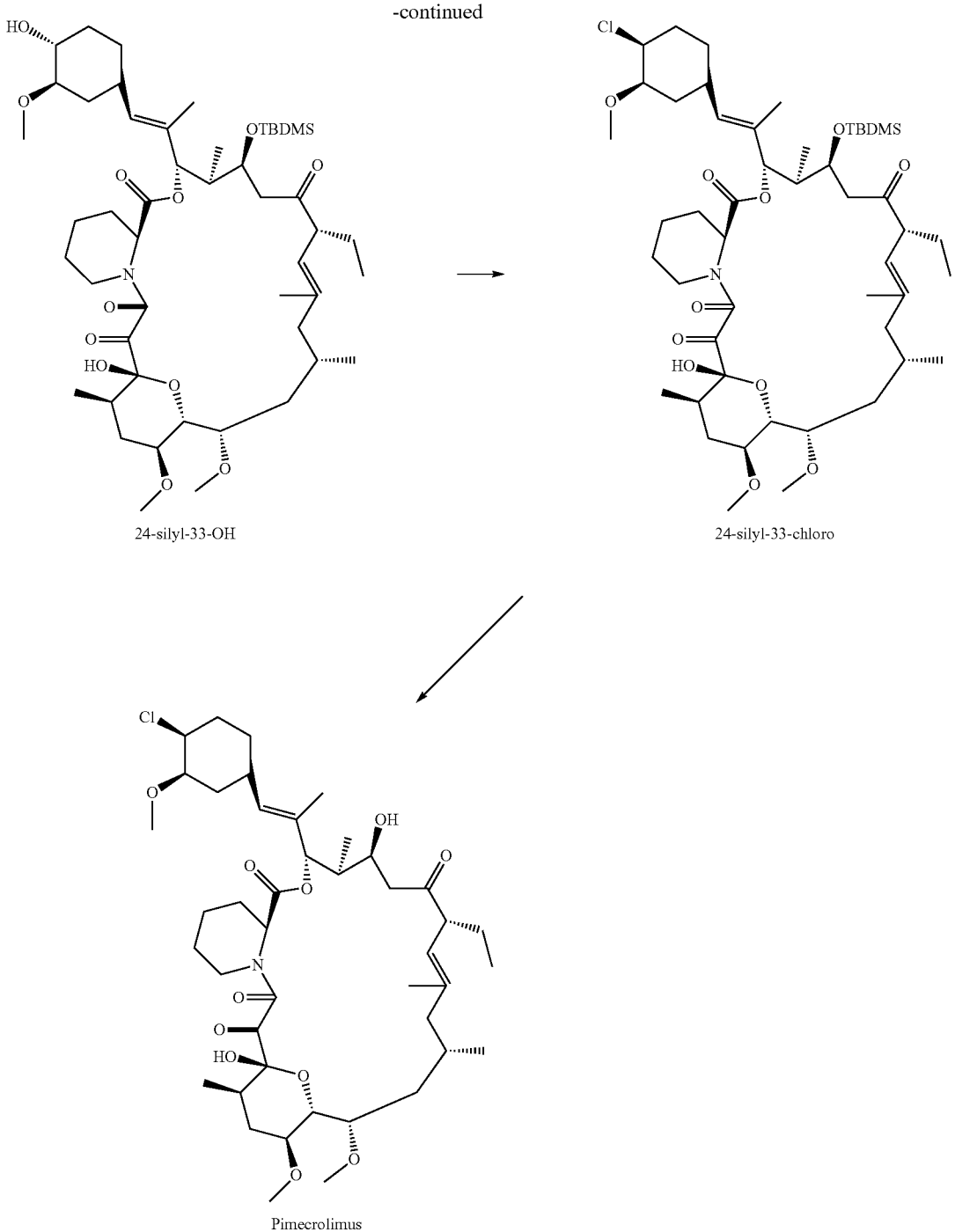

24-silyl-33-OH 24-silyl-33-chloro

Pimecrolimus

From a structural point of view, pimecrolimus is the 33-epi-chloro derivative of ascomycin. As described in EP427680, the simultaneous presence—in the structure of ascomycin—of two secondary hydroxyl groups in position 24 and in position 33, requires the protection of the hydroxyl in position 24 before substituting the second hydroxyl in position 33 with an atom of chlorine.

In order to obtain the monoprotection of the hydroxyl in position 24 of ascomycin, such synthesis process provides for the preparation of 24,33-disilyl derivative and the subsequent selective removal of the silyl ester in position 33.

The high ratio between the silylating agent and the substrate and the non-complete selectivity of the subsequent step of deprotection requires carrying out two chromatographic purifications on the column of silica gel (Baumann K., Bacher M., Damont A., Hogenauer K., Steck A. *Tetrahedron*, (2003), 59, 1075-1087).

The general yields of such synthesis process are not indicated in literature; an experiment by the applicant revealed that such yields amount to about 16% molar starting from ascomycin.

Other synthesis processes were recently proposed as alternatives to the synthesis of EP427680.

In particular, the International patent application WO2006040111 on behalf of Novartis provides for the direct substitution of the hydroxyl in position 33 of ascomycin with an atom of chlorine and a second alternative, described in the international patent application WO2006060614 on behalf of Teva, uses—as a synthetic intermediate—a sulfonate derivative in position 33 of ascomycin. Both the proposed synthetic alternatives are not entirely satisfactory in that in WO2006040111 the proposed halogenating agents (chlorophosphorane and N-chlorosuccinimide) are not capable, according to the same authors, of regioselectively substituting the hydroxyl function in position 33, while in WO2006060614 the quality characteristics of the obtained product are, even after chromatographic purification and/or crystallisation, low for a product to be used for pharmaceutical purposes (i.e. purity of 96% as described in the experimental part).

Generally, purified enzymatic systems may be used for the organic synthesis of polyfunctional molecules (Wang Y-F, Wong C-H. *J Org Chem* (1988) 53, 3127-3129; Santaniello E., Ferraboschi P., Grisenti P., Manzocchi A. *Chem. Rev.* (1992), 92(5), 1071-140; Ferraboschi P., Casati S., De Grandi S., Grisenti P., Santaniello E. *Biocatalysis* (1994), 10(1-4), 279-88); WO2006024582). WO2007103348 and WO2005105811 describe the acylation of rapamycin in position 42 in the presence of lipase from *Candida antartica*.

SUMMARY OF THE INVENTION

Thus, an object of the present invention are alternative processes for preparing pimecrolimus starting from ascomycin exploiting the selectivity characteristics of the purified enzymatic systems particularly regarding the possibility of selective functionalization of the hydroxyl groups present in position 24 and 33 of ascomycin. Such method represents the first example of chemoenzymatic synthesis for preparing pimecrolimus.

In particular, the process according to the present invention allows obtaining pimecrolimus starting from ascomycin with a yield of about 30% molar, i.e. with a yield higher by about 87.5% with respect to the yield obtainable according to the process outlined in EP427680.

DESCRIPTION OF THE INVENTION

The object of the present invention are methods for alternative synthesis of pimecrolimus, comprising the selective enzymatic functionalization of the hydroxyl in position 33 or in position 24 of ascomycin.

Enzymes available in the market, such as for example lipase from *Candida antartica* (CAL B; E.C.3.1.1.3), from *Candida cylindracea* (CCL, E.C.3.1.1.3), from porcine pancreas (PPL; E.C.3.1.13) and from *Pseudomonas cepacia* (PFL, E.C.3.1.13) were evaluated thorough screening carried out both under hydrolysis and alcoholysis conditions using—as a substrate—ascomycin 24, 33 diacetate (compound V of scheme 3), and under transesterification conditions using—as substrate-ascomycin.

Thus, it was surprisingly discovered that only the lipase from *Candida antartica* (in the forms of free enzymes available in the market or as enzymes immobilized on a polymeric resin; the latter form also being referred to as CAL B) under the irreversible transesterification conditions (conditions that provide for the use of vinyl acetate as an acylating agent and tert-butyldimethylether as a solvent), is capable of selectively acylating position 33 of ascomycin in a quantitative manner within 80 hours, just like only the lipase from *Candida antartica*, and in particular CAL B, operating under conditions of alcoholysis on 24,33-diacetate of ascomycin, surprisingly proved to be capable of chemoselectively leading to the corresponding 24-monoacetate of ascomycin (compound VI of scheme 3).

Thus, an object of the present invention are processes for preparing pimecrolimus, characterised in that they comprise a step of acylation and/or enzymatic alcoholysis with lipase from *Candida antartica*, where preferably said lipase from *Candida antartica* is CAL B (E.C.3.1.1.3.).

Furthermore, an object of the present invention are methods of synthesis of pimecrolimus, comprising a step of selective enzymatic alcoholysis of esters in position 33 of ascomycin (preferably of $C_1$-$C_4$ esters) or of silylated derivatives of such esters, and more in detail of the derivatives thereof such as 33-acyl-24 silyl ascomycin and the diacetylated ascomycin in positions 24 and 33, by a lipase from *Candida antartica*, preferably lipase CAL B (E.C.3.1.1.3.)

Such method represents the first example of chemoenzymatic synthesis for preparing pimecrolimus. With respect to the chemical synthesis previously described in literature, this method has the advantage of using, on a polyfucntional macromolecule such as ascomycin or derivatives thereof, non-extreme reaction conditions (for example pH and temperature), thus minimizing the degradation of the product itself.

Use of the lipase from *Candida antartica* bonded to a polymeric matrix (CAL B), to obtain protection/deprotection of the hydroxyl functions present in position 33 and 24 of ascomycin represents a further advantage of this synthesis, in that the use of a supported enzyme not only considerably simplifies the reaction workup, but also allows use thereof in several use cycles. As a matter of fact, it is known that—contrary to the non-supported lipase—CAL B is not only insoluble in most organic solvents and in water, thus allowing easy recovery thereof from the reaction medium through simple filtration, but that such type of supported lipase is also more stable from an enzymatic activity point of view (Ferraboschi P., Grisenti P., Pengo D., Prestileo P.. *Biocatalysis and Biotransformation* (2006), 24(3), 209-213; Heldt-Hansen, Hans Peter; Ishii, Michiyo; Patkar, Shamkant A.; Hansen, Tomas T.; Eigtved, Peter.Novo Ind. A/S, Bagsvaerd, Den. ACS Symposium Series (1989), 389 (*Biocatal. Agric. Biotechnol.*), 158-72).

Another object of the present invention is a method for the synthesis of pimecrolimus, comprising the following steps: a) selective enzymatic acylation of the hydroxyl in position 33 of ascomycin; b) conversion of the 33-acylated derivative thus obtained in the corresponding 24-tert-butyldimethylsilyl ether; c) enzymatic removal (alcoholysis) of the acyl in position 33 of the compound prepared in step b) to obtain the 24-tert-butyldimethylsilyl ether of ascomycin; d) substitution of the hydroxyl in 33 of 24-tert-butyldimethylsilyl ether of ascomycin, with an atom of chlorine to obtain the derivative 24-tert-butyldimethylsilyl-33-epi-chloro ascomycin; and lastly e) the removal of the tert-butyldimethylsilyl ether in position 24.

In particular, the steps indicated above are carried out as follows:

a) the chemoselective esterification reaction of ascomycin on the hydroxyl in position 33 is carried out characteristically by using—as an enzyme—the lipase from *Candida antartica* (CAL B, E.C.3.1.1.3) in suitable organic solvent, selected from among aprotic organic solvents with a coefficient of partition (log P) exceeding 0.5, such as for example toluene, n-hexane, n-heptane, dichloromethane, chloroform and tert-butyldimethylether, in the presence of an acylating agent such as an activated ester of the vinyl ester or $C_1$-$C_8$ trifluoroethyl ester type, preferably trifluoroethyl acetate or vinyl acetate. Such esterification reaction is carried out using a relative ratio between mg of ascomycin and units of CAL B comprised between 0.1 and 1, preferably 0.4, under stirring at a temperature comprised between 15 and 50° C., preferably 30° C. The relative molar ratio between ascomycin and activated ester is comprised between 1 and 6 preferably 4.5. The concentration of the substrate on which such transesterification reaction is carried out is comprised between 0.01 and 0.1 molar.

b) The preparation reaction of 24-tert-butyldimethylsilylether-33-acyl ascomycin derivative is obtained in the presence of a silylating agent, such as tert-butyldimethylsilyl chloride or tert-butyldimethylsilyl triflate, used in a relative molar ratio comprised between 1/2 and 1/7, preferably 1/5, in the presence of an organic base, such as for example imidazole, pyridine or 2,6-lutidine, preferably 2,6-lutidine. The relative molar ratio between silylating agent and organic base is comprised between 1/1 and 1/4 preferably 1/3. The reaction is carried out in un aprotic organic solvent, such as for example dichloromethane or tetrahydrofuran, operating in the range of concentration of 0.02-0.15 molar, preferably 0.04 molar, at a temperature comprised between 0° C. and 40° C., preferably 25° C.

c) The enzymatic reaction for preparing 24-tert-butyldimethylsilylether of ascomycin (intermediate 24-silyl-33-OH; compound III of scheme 2), i.e. the alcoholysis reaction in position 33, is carried out characteristically using—as an enzyme—the lipase from *Candida antartica* (CAL B, E.C.3.1.1.3). The organic solvent used is selected from among aprotic solvents with a log P exceeding 0.5 such as for example tert-butylmethylether, dichloromethane or toluene, preferably tert-butylmethylether, in the presence of a $C_1$-$C_8$ primary aliphatic alcohol, preferably n-octan-1-ol. Such alcoholysis reaction is carried out using a relative ratio between mg of 24-tert-butyldimethylsilylether-33-acetyl ascomycin derivative and units of CAL B comprised between 0.1 and 0.5, preferably 0.25, operating under stirring at a temperature comprised between 15° C. and 60° C., preferably 40° C. The relative molar ratio between substrate and the primary aliphatic alcohol is comprised between 0.1 and 0.4, preferably 0.2. The reaction is carried out at the concentration of the substrate comprised between 0.01 and 0.1 molar, preferably 0.02 molar.

d) The preparation of 24-tert-butyldimethylsilylether-33-epi-chloro ascomycin (intermediate 24-silyl-33-Chloro; compound IV of scheme 2) is carried out characteristically using—as a reagent—dichloro-triphenylphosphorane or N-chlorosuccinimide; the reagent is used at a relative molecular ratio with the substrate comprised between 1.2 and 1.8, preferably 1.6, in an aprotic solvent such as for example toluene, n-hexane or dichloromethane, preferably toluene. Carried out is a concentration of the substrate comprised between 0.05 and 0.1 molar, preferably 0.07 molar, in the temperature range comprised between 25° C. and 80° C., preferably at 60° C.

e) The removal of the tert-butilsilyl ether in position 24 to obtain pimecrolimus is carried out by means of acid catalysis that may be obtained using monoprotic inorganic acids such as fluorhydric acid or hydrochloric acid or organic acids such as p-toluenesulfonic acid monohydrate or methanesulfonic acid, preferably p-toluenesulfonic acid monohydrate, using a molar ratio between substrate and acid comprised between 1:0.3 and 1:1, preferably 1:0.4, operating at a temperature range comprised between 15 and 40° C., preferably 25° C., over a reaction time comprised between 24 and 72 hours. Such reaction is carried out by operating at a molar concentration of the substrate comprised between 0.05 and 0.2 M, preferably at the concentration of 0.12 M, using—as reaction solvent—mixtures of aprotic and protic solvents used at a relative volumetric ratio comprised between 2/8 and 8/2. Examples of aprotic solvents useable in such step are dichloromethane and hydrocarbons or mixtures of linear or branched $C_5$-$C_7$ hydrocarbons, preferably dichloromethane. Examples of protic solvents useable in this step are straight or branched-chain $C_1$-$C_4$ alcohols, preferably methanol.

A preferred synthesis according to the method described above, is schematized in the following scheme 2:

Scheme 2: synthesis of pimecrolimus for enzymatic transesterification of ascomycin.

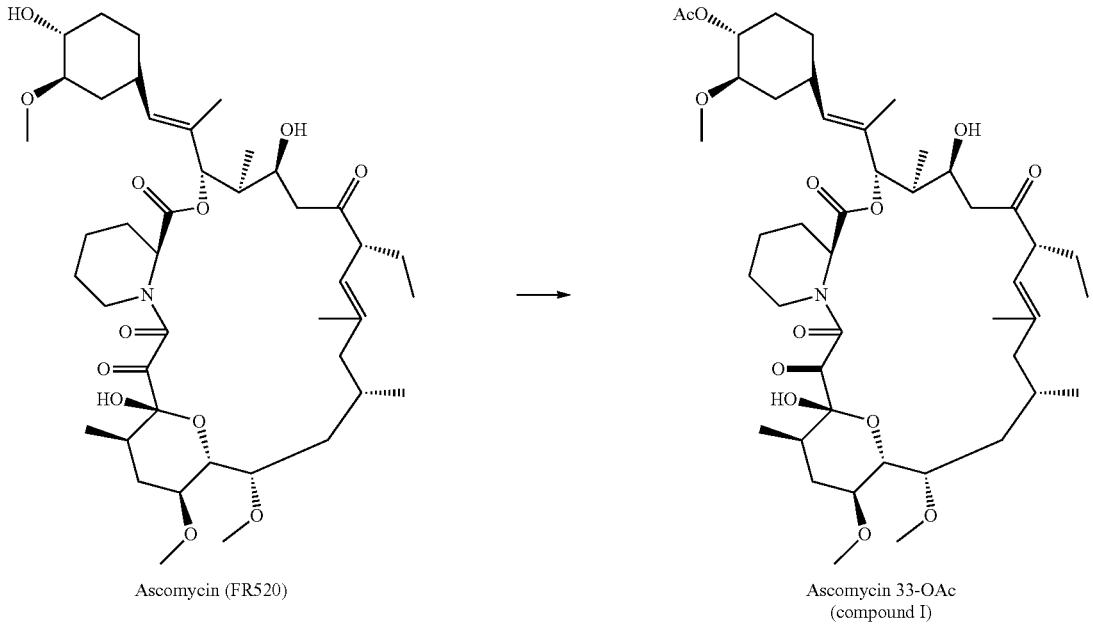

Ascomycin (FR520)

Ascomycin 33-OAc (compound I)

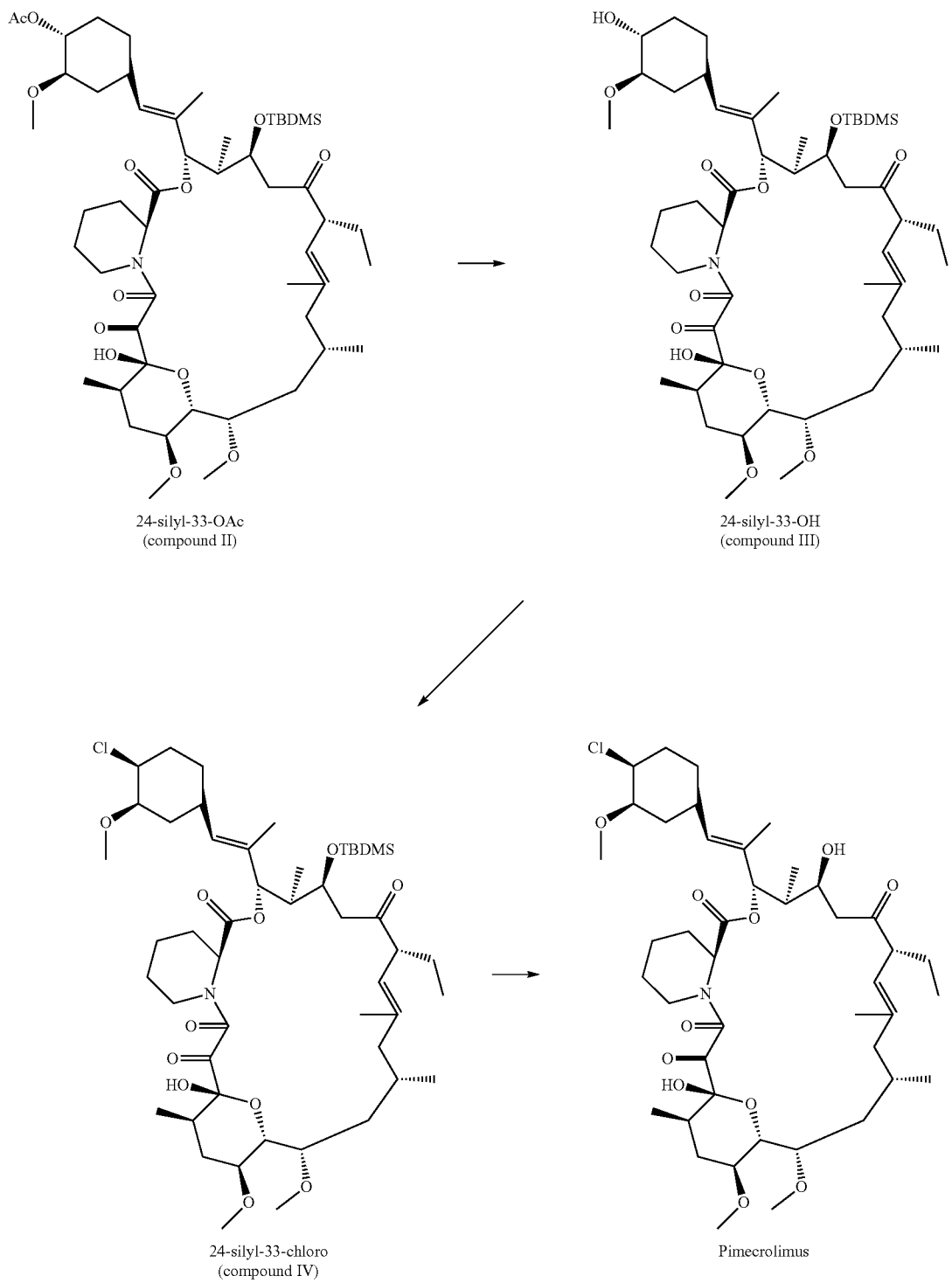

24-silyl-33-OAc
(compound II)

24-silyl-33-OH
(compound III)

24-silyl-33-chloro
(compound IV)

Pimecrolimus

Carried out on the initial product, i.e. ascomycin, is an irreversible transesterification catalysed by the lipase from *Candida antartica* (CAL B) using vinyl acetate as an acylating agent and tert-butyldimethylether (TBDME) as a solvent. This allows obtaining selective acetylation of position 33 of ascomycin in a quantitative manner in 80 hours.

The reaction product obtained (intermediate ascomycin 33-OAc; compound I of scheme 2), without any purification, was converted into the corresponding 24-tert-butyl-dimethyl-silyl ether (intermediate 24-silyl-33-OAc; compound II of scheme 2) with tert-butyldimethylsilyl triflate in dichloromethane and 2,6-lutidine in 0.5 hours, with a yield of 75%.

After chromatographic purification on silica gel, the acetate in position 33 of the intermediate 24-silyl-33-OAc was removed, still using CAL B under conditions of alcoholysis, i.e. using octan-1-ol in tert-butyldimethylether providing the 24-silyl ether derivative of ascomycin (compound III of scheme 2) with yields comprised between 80 and 100%.

This intermediate was converted into the final product substituting the hydroxyl in with an atom of chlorine, through the reaction with dichlorotriphenylphosphorane. The intermediate 24-silyl-33-chloro (compound IV of scheme 2) was obtained after chromatographic purification.

Lastly, the removal of the silyl ether in position 24 using p-toluenesulfonic acid monohydrate in dichloromethane/methanol allows obtaining pimecrolimus starting from ascomycin with overall yields of about 30% molar.

Thus, there is a higher yield with respect to the synthesis of pimecrolimus described previously and, in particular, a yield higher by 87.5% with respect to the yield obtainable according to the process described in EP427680. As a matter of fact, the experimental test carried out by the applicant, regarding the description outlined in EP427680, confirmed overall conversion yields of 16%, as indicated in the comparative example 4. In particular, particularly penalising for the overall yields of the process were the stop for the deprotection of ter-butyldimethylsilylether groups in position 24 and 33 carried out under the conditions described in example 1b and 47 (45-50% yield) of the abovementioned patent and the halogenations as described in example 1 (50-60% yield). The compound 24-silyl-33-OAc (compound II of scheme 2), i.e. compound 24-tert-butyldimethylsilyl-33-acetyl-ascomycin is a compound that has never been described in literature and it was synthesized and characterised for the first time in the present invention.

Thus, a further aspect of the present invention is represented by compound 24-tert-butyldimethylsilyl-33-acetyl-ascomycin, obtained as an intermediate in the enzymatic synthesis process of pimecrolimus.

Another subject of the present invention lies in the use—as an intermediate in the synthesis of pimecrolimus—of the compound 24-tert-butyldimethylsilyl-33-acetyl-ascomycin.

Another object of the present invention is a method for the synthesis of pimecrolimus, comprising the following steps: a') preparing acetylated ascomycin in positions 24 and 33; b') enzymatic removal (alcoholysis) of the acyl in position 33 to obtain monoacetylated ascomycin at position 24; c') substitution of the hydroxyl in 33 of ascomycin with an atom of chlorine to obtain the compound 24-acetate-33-epi-chloro ascomycin; d') the removal of the acetate in position 24.

In particular, the steps indicated above are performed as follows:

a') the preparation of ascomycin 24,33-diacetate (intermediate 24,33 diacetate; compound V of scheme 3) is characteristically carried out using—as acylating agents—acetyl chloride or acetic anhydride, at a relative molar ratio with the substrate comprised between 3 and 6, preferably 4.5, in the presence of N,N-dimethylaminopyridine (DMAP), which is used in a relative ratio with the acylating agent comprised between 1.0 and 1.2, preferably 1.0. The reaction is carried out using—as a solvent—an organic base such as pyridine or triethylamine, preferably pyridine, operating at the concentration of the substrate comprised between 0.08-0.5 molar, preferably 0.1 molar. The temperature of this reaction may be comprised between −5° C. and 25° C., preferably at the temperature of 0° C.

b') the enzymatic reaction (alcoholysis) for preparing 24-acetyl-ascomycin (intermediate 24-acetate-33-OH; compound VI of scheme 3) starting from ascomycin 24,33-diacetate (intermediate 24,33-diacetate), is carried out characteristically using—as an enzyme—lipase from *Candida antartica* (CAL B, (E.C.3.1.1.3.)) in a suitable organic solvent selected from among aprotic solvents with a log P exceeding 0.5, such as for example tert-butylmethylether, dichloromethane or toluene, preferably tert-butylmethylether, in the presence of the primary C1-C8 aliphatic alcohol, preferably n-octan-1-ol. Such reaction is carried out using a relative ratio between mg of ascomycin 24,33-diacetate and units of CAL B comprised between 0.1 and 0.5, preferably 0.23, operating under stirring at a temperature comprised between 15° C. and 60° C., preferably 30° C. The relative molar ratio between the primary aliphatic alcohol and substrate is comprised between 0.2 and 0.8, preferably 0.5. The reaction is carried out at the concentration of the substrate comprised between 0.01 and 0.1 molar, preferably 0.02 molar.

c') the preparation of 24-acetyl-33-epi-chloro ascomycin (intermediate 24-acetate-33-chloro; compound VII of scheme 3) starting from 24-acetyl ascomycin is characteristically carried out using polymerically supported triphenylphosphine, available in the market (at a titre of about 3 mmoles of triphenylphosphine per gram of styrene and divinylbenzene copolymer), in a molar ratio (calculated on the triphenylphosphine content) comprised between 2.0 and 3.0 with respect to the substrate, preferably 2.3. The reaction is carried out in a $C_1$-$C_2$ chlorinated solvent such as carbon tetrachloride alone, or hexachloroethane in the presence of another nonpolar aprotic organic solvent such as for example linear or branched $C_5$-$C_8$ aliphatic hydrocarbons or aromatic hydrocarbons such as for example toluene or xylene, preferably carbon tetrachloride, operating at a temperature comprised between 60° C. and 85° C., preferably 77° C. at the concentration of the substrate comprised between 0.05 and 0.20 molar, preferably 0.1 molar.

d') the removal of the acetate in position 24 to obtain pimecrolimus is carried out using an acid catalysis operating at a temperature range comprised between 5 and 40° C. in a polar protic solvent such as for example linear or branched $C_1$-$C_8$ alcohols, preferably methanol, at the concentration of the substrate comprised between 0.05 and 0.2 M. The acid catalyst useable in this step may be an inorganic monoprotic acid such as fluorhydric acid or hydrochloric acid or an organic acid such as for example the p-toluenesulfonic monohydrate acid or methanesulfonic acid, preferably hydrochloric acid. The molar ratio between substrate and optimal acid in this step is comprised between 1:5 and 1:20, preferably 1:13.

Advantageously, the use of supported triphenylphosphine, in the substitution reaction of hydroxyl in position 33 with an atom of chlorine of step c'), allows considerable simplification of the workup of such step of synthesis which is actually reduced to simple filtration. A further advantage of such synthetic modification lies in the fact that the supported oxidized triphenylphosphine recovered at the end of the reaction may be reutilised, after regeneration using trichlorosilane (registry number 10025-778-2; Regent S. L , Lee D. P. *Journal of Organic Chemistry*, (1975), 40, 1669-1670), in the same process.

The synthesis according to the method described above, is schematized in the following scheme 3:
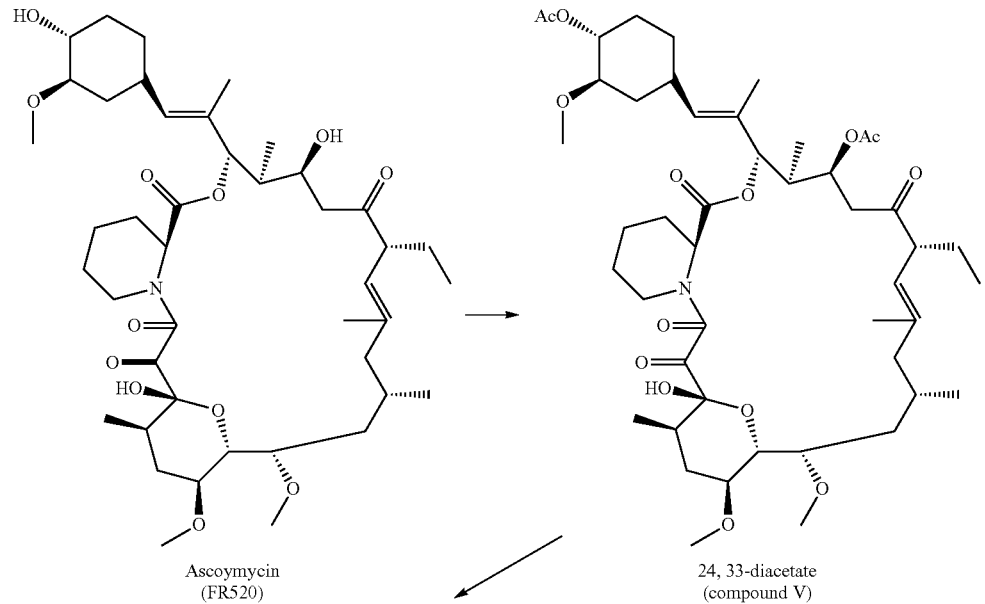
Ascoymycin (FR520)
24, 33-diacetate (compound V)
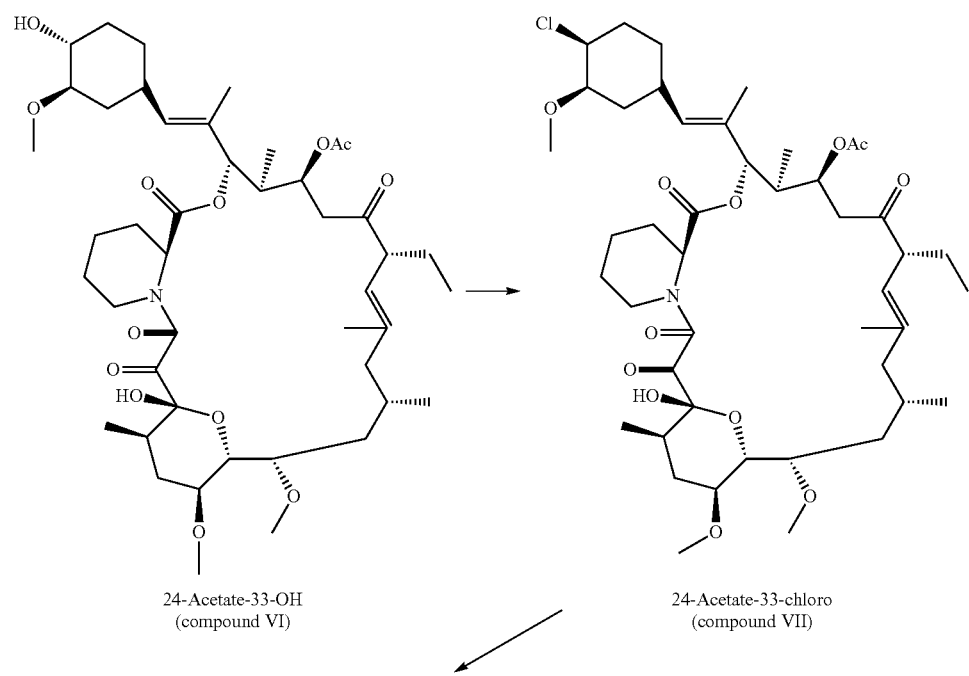
24-Acetate-33-OH (compound VI)
24-Acetate-33-chloro (compound VII)

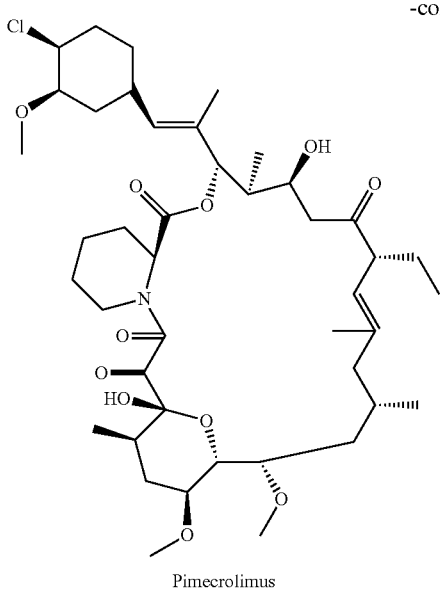

Pimecrolimus

A preferred synthesis according to the method described above, provides for the reaction of ascomycin with acetic anhydride and dimethylaminopyridine (DMAP) in pyridine at 0° C. The 24,33-diacetate derivative was prepared in 1 hour (compound V of scheme 3; 95% yield).

It was surprisingly discovered that, also on this substrate, the lipase from *Candida antartica* (CAL B; E.C.3.1.1.3), operating under conditions of alcoholysis, is capable of chemoselectively leading to the corresponding 24-monoacetate of ascomycin (compound VI of scheme 3).

Thus, 24, 33-diacetate (compound V) of ascomycin was converted into 24-monoacetate (24-acetate-33-OH; compound VI) during a catalysed transformation from CAL B with octan-1-ol into tert-butyldimethylether (TBDME) (100%, in 5 hours)

The chlorine in position 33 was introduced by reaction with supported triphenylphosphine and carbon tetrachloride with yields of 40% to obtain the intermediate 24-acetate-33-chloro (compound VII of scheme 3).

The use of supported triphenylphosphine in this step of synthesis as an alternative to the use of triphenylphosphine, previously described in literature, to introduce chlorine on the protected ascomycin on the hydroxyl in position 24, allowed—considering the same conversion yields—considerably simplifying the reaction workup which, in the case of supported triphenylphosphine, is carried out by simply filtering the reaction mixture and evaporating the filtrate under vacuum. Such reagent also has the advantage of allowing reutilization, after regeneration with trichlorosilane, in the same process.

The removal of the acetate in position 24 with 3N HCl in methanol at ambient temperature (yields of 40%) obtained pimecrolimus with characteristics identical to a reference sample and overall yields of 13% (Scheme 3). The process intermediates ascomycin 24,33-diacetate (compound V), ascomycin 24-monoacetate (compound VI) and ascomycin 24-acetate-33-epi-chloro (compound VII) are not described in literature and they were synthesized and characterized for the first time in the present invention.

Thus, a further aspect of the present invention is represented by the ascomycin 24,33-diacetate, ascomycin 24-monoacetate and ascomycin 24-acetate-33-chloro compounds, obtained as intermediates in the enzymatic synthesis process of pimecrolimus.

Other objects of the present invention are the uses of pimecrolimus—of the ascomycin 24,33-diacetate, ascomycin 24-monoacetate and ascomycin 24-acetate-33-chloro compounds as intermediates in the synthesis.

The following examples illustrate the invention, without restricting it in any manner whatsoever.

EXAMPLES

Materials and Methods

In the following examples, the $^1$H-NMR (500 MHz) analysis were recorded in deuterochloroform on Bruker AM500 instrument; the indicated spectra values are in ppm (δ) and they refer to the diagnostic peaks of the main isomer.

The IR analysis were recorded on Perkin Elmer FT IR (Mod. Spectrum One) instruments equipped with ATR. The polarimetric analyses were carried out on Perkin Elmer (Mod.343) instruments. The mass spectra were recorded on Finnigan LCQ Deca Termoquest spectrometer instruments (Ion trap; ESI positive) using the direct infusion technique.

The indicated differential calorimetry scanning (DSC) values were recorded on Perkin Elmer (Mod. DSC7) instrument at a heating value of 5° C./min. The lipase from *Candida antartica* (CAL B 2 U/mg; E.C.3.1.1.3), from *Candida cylindracea* (CCL 15-25 U/mg; E.C.3.1.1.3), from porcine pancreas (PPL ≥200 U/mg; E.C.3.1.13), from *Pseudomonas cepacia* (PFL 50 U/mg; E.C.3.1.13) and the supported triphenylphosphine (about 3.2 mmoles/g of triphenylphosphine) were acquired by Fluka. The ascomycin used as initial reagent of the synthesis was prepared by Poli Industria Chimica SpA, Quinto de Stampi, Rozzano (MI), Italy.

Example 1

Preparation of the 33-acetyl Derivative of Ascomycin (Compound I of Scheme II)

Lipase from *Candida antarctica* (CAL B, Novozym 435) [0.140 g (2 U/mg) FLUKA] was added to a solution of ascomycin (100 mg; 0.126 mmol) in toluene (8 ml) and vinyl acetate (4.5 eq; 0.473 g). The reaction is kept under stirring at the temperature of 30° C. for 80 hrs then the enzyme is taken away for filtration and the filtrate is concentrated at low pressure to obtain 105 mg of 33-acetyl ascomycin.

A sample of such intermediate was purified for analytical purposes by chromatography on silica gel (n-hexane/acetone=8/2 v/v as eluents) and thus crystallised by acetone/water.

The following analysis were carried out on such sample: $^1$H-NMR (500MHz) δ: 2.10 (CH$_3$CO), 3.92 and 4.70 (24CH and 33CH); IR (cm$^{-1}$): 3484.245, 2935.287, 1735.331, 1649.741, 1450.039, 1372.278; DSC: endotherm at 134.25° C.; $[\alpha]_D$=−74.0° (c=0.5 CHCl$_3$).

Spectrum of MS (ESI+): m/z: 856.4 (M+23; 100.0%)

Elementary analysis calculated for $C_{45}H_{71}NO_{13}$: C 64.80%; H, 8.58%; N, 1.68%; O, 24.94%

Elementary analysis found: C 64.78%; H, 8.54%; N, 1.59%; O, 24.89%

Preparation of the
24-tert-butyldimethylsilylether-33-acetyl Derivative
of Ascomycin (Intermediate 24-silyl-33-Oac;
Compound II of Scheme 2)

2,6-lutidine (0.290 g; 2.7 mmolels) and tert-butyldimethylsilyl triflate (0.238 g; 0.9 mmoles) are added to a solution of 33-acetyl derivative of ascomycin (150 mg; 0.18 mmoles) in dichloromethane (5 ml). The reaction is left under stirring at ambient temperature for 30 minutes. After this period the reaction mixture is washed with a solution saturated with sodium bicarbonate (5 ml) and organic phase obtained is washed in sequence with HCl 0.1N (5 ml 3 times) and with a solution at 30% of NaCl (5 ml). The organic phase is anhydrified on sodium sulphate, filtered and concentrated to residue under vacuum to obtain 128 mg of product.

Spectrum of MS (ESI +): m/z: 970.5 (M+23; 100.0%)

$^1$H-NMR (500 MHz) δ: 0.05 and 0.06 ((CH$_3$)$_2$Si), 0.90 ((CH$_3$)$_3$C-Si), 2.10 (CH$_3$CO), 4.70 (33CH)

IR (cm$^{-1}$): 3462.948, 2934.450, 1739.236, 1649.937

Elementary analysis calculated for $C_{51}H_{85}NO_{13}Si$: C 64.59%; H, 9.03%; N, 1.48%; 0, 21.93%

Elementary analysis found: C 64.50%; H, 9.05%; N, 1.41%; O, 21.88%

DSC=endoderma a 236,43° C. $[\alpha]_D$=−81.4° (c=0.5 CHCl$_3$).

Preparation of 24-tert-butyldimethylsilylether of
Ascomycin (Intermediate 24-silyl-33-OH;
Compound III of Scheme 2)

n-octan-1-ol (0.035 g; 0.265 mmoles) and CAL B (Novozym 435) [0.100 g (2 U/mg) FLUKA] are added to a solution of 24-tert-butyldimethylsilylether-33-acetyl derivative of ascomycin (50 mg; 0.053 mmoles) in tert-butylmethylether (4 ml). The reaction is kept under stirring at the temperature of 40° C. for 120 hours. After this period the reaction mixture is filtered and the filtrate is evaporated to residue under vacuum to obtain a reaction raw product which is purified by chromatography on silica gel: 44 mg of product (0.048 mmoles) are recovered through elution with petroleum ether/acetone 7/3.

The chemical/physical properties of the obtained product match those of a reference sample obtained according to patent EP427680.

Preparation of
24-tert-butyldimethylsilylether-33-epi-chloro
Ascomycin (Intermediate 24-silyl-33-chloro;
Compound IV of Scheme 2)

A solution of 24-silyl FR520, i.e. 24-silyl ascomycin (165 g; 0.18 moles) in anhydrous toluene (1.4 liters) and pyridine (50 ml) is added to a suspension of dichlorotriphenylphosphorane (99.95 g) in anhydrous toluene (1.1 liters), under stirring at ambient temperature (20-25° C.) in inert atmosphere.

After adding, the reaction mixture is heated at the temperature of 60° C. for 1 hour.

After this period the temperature of the reaction mixture is taken to 25° C. and thus the organic phase is washed in sequence with water (1 time with 1 L) and with an aqueous solution of NaCl at 10% (4 times with 1 L each time), then it is anhydrified on sodium sulphate, filtered and concentrated under vacuum to obtain about 250 g of a moist solid of toluene. Such residue product is retaken with n-hexane (500 ml) and then evaporated to dryness (in order to remove the toluene present). The residue product is diluted in n-hexane (500 ml) under stirring at ambient temperature for about 45 minutes and then the undissolved solid taken away for filtration on buckner (it is the sub-product of dichlorophosphorane).

The filtrate is concentrated at low pressure to obtain 148.6 g of a solid which is subsequently purified by chromatography on silica gel (elution with n-heptane/acetone=9/1) to obtain 123 g (0.13 moles) of product.

The chemical/physical properties of the obtained product match those described in literature (EP427680).

Preparation of the Pimecrolimus from
24-tert-butyldimethylsilylether-33-epi-chloro
Ascomycin The intermediate 24-silyl-33 chloro (123 g; 0.13 Moles; compound IV of scheme 2) is dissolved under stirring at ambient temperature in a dichloromethane/methanol mixture=1/1=v/v (1.1 liters) then p-toluenesulfonic acid monohydrate (10.11 g) is added.

The reaction is kept under stirring at the temperature of 20-25° C. for 72 hours, thus a solution of water (600 ml) and sodium bicarbonate (4.46 g) is added to the reaction mixture. The reaction mixture is kept under stirring at ambient temperature for 10 minutes, the organic phase is then prepared and washed with an aqueous solution at 10% of sodium chloride (600 ml).

The organic phase is anhydrified on sodium sulphate, filtered and concentrated under vacuum to obtain 119 g of raw pimecrolimus. Such raw product is purified by chromatography on silica gel (n-hexane/acetone as eluents) and thus crystallised by ethyl acetate, cyclohexane/water to obtain 66 g (81.5 mmoles) of purified pimecrolimus.

The chemical/physical data obtained matches the data indicated in literature.

Example 2

Preparation of Ascomycin 24,33-diacetate
(Intermediate 24, 33-diacetate; Compound V of
Scheme 3)

DMAP (4.5 eq; 0.136 g) and acetic anhydride (4.5 eq; 0.114 g) are added to a solution of ascomycin (200 mg; 0.25 mmoles) in pyridine (2.5 ml), under stirring at the temperature of 0° C.

The reaction is kept under stirring for 1.5 hours at the temperature of 0° C. then it is diluted with water and it is extracted with ethyl acetate (3 times with 5 ml). The organic extracts are washed with HCl 0.5 N (5 times with 10 ml), anhydrified on $Na_2SO_4$ concentrated under vacuum.

The residue product was purified by chromatography on silica gel (n-hexane/acetone 8/2 v/v as eluent) to obtain ascomycin 24,32-diacetate (210 mg; 0.24 mmoles).

We carried out the following analysis on such purified sample:
$^1$H-NMR (500 MHz) δ: 2.02 and 2.06 (2 $CH_3CO$), 5.20 and 4.70 (24CH and 33CH);
IR ($cm^{-1}$): 3462.749, 2935.824, 1734.403, 1650.739, 1449.091, 1371.079.
DSC: endothermic peak at 234.10° C.; $[α]_D=-100.0°$ (C=0.5 $CHCl_3$).
Spectrum of MS (ESI+): m/z: 898.4 (100.0%; m+23)
Elementary analysis calculated for $C_{47}H_{73}NO_{14}$: C 64.44%; H 8.40%; N 1.60%; O 25.57%
Elementary analysis found: C 64.55%; H 8.44%; N 1.61%; O 25.40%

Preparation of the 24-acetyl Ascomycin
(Intermediate 24-acetate-33-OH; Compound VI of Scheme 3)

Lipase from *Candida antartica* (CAL B Novozym 435) [1.1 g (2 U/mg) FLUKA] is added to a solution of ascomycin 33,24-diacetate (500 mg; 0.57 mmol) in TBDME (25 ml) and n-octan-1-ol (4.5 eq; 0.371 g). The reaction is kept under stirring at 30° C. for 100 hours, then the enzyme is taken away for filtration and the obtained filtrate is concentrated under low pressure to obtain 425 mg (0.51 mmoles) of product.

A sample was purified for analytical purposes by chromatography on silica gel (n-hexane/acetone=7:3 v/v as eluents) and thus crystallised by acetone/water.

We carried out the following analysis on such purified sample: $^1$H-NMR (500MHz) δ: 2.05 ($CH_3CO$); IR ($cm^{-1}$): 3491.528, 2935.860, 1744.728, 1710.227, 1652.310, 1448.662, 1371.335. DSC: endothermic peak at 134.68° C.; $[α]_D=-102.7°$ (c=0.5 $CHCl_3$)
Spectrum of MS (ESI +): m/z: 856.4 (M+23; 100.0%)
Elementary analysis calculated for $C_{45}H_{71}NO_{13}$: C 64.80%; H, 8.58%; N, 1.68%; O, 24.94%
Elementary analysis found: C 64.71%; H, 8.49%; N, 1.60%; O, 24.97%

Preparation of the 24-acetyl-33epi-chloro Ascomycin
(Intermediate 24-Acetate-33-chloro; Compound VII of Scheme 3)

Supported triphenylphosphine (0.335 g; 1.1 mmoles) is added to a solution of 24-acetyl ascomycin (400 mg; 0.48 mmoles) in carbon tetrachloride (5 ml). The reaction mixture is kept under reflux for 3 hours then it is cooled at ambient temperature. The obtained suspension is filtered and the filtrate is concentrated to residue under vacuum to obtain 0.45 g of reaction raw product which is purified by chromatography on silica gel: 163 mg (0.19 mmoles) of product are obtained by elution with petroleum ether/acetone=90/10.

$^1$H-NMR δ: 2.08 ($CH_3CO$); 4.60 (33CH); IR ($cm^{-1}$) =3464.941, 2934.360, 1738.993, 1650.366, 1450.424, 1371.557; DSC: endothermic peak at 231.67° C. $[α]_D=-75.2°$ (c=0.5 $CHCl_3$)
Spectrum of MS (ESI+): m/z: 874.3 (M+23; 100.0%)
Elementary analysis calculated for $C_{45}H_{70}ClNO_{12}$: C 63.40%; H, 8.28%; Cl, 4.16%; N, 1.64%; 0, 22.52%
Elementary analysis found: C 63.31%; H, 8.30%; Cl, 4.05%; N, 1.58%; O, 22.42%.

Preparation of Pimecrolimus from
24-acetyl-33-epi-chloro Ascomycin

A solution of 24-acetyl-33-epi-chloro ascomycin (200 mg; 0.23 mmoles; compound VII) in methanol (2 ml) and HCl 3N (1 ml) is stirred at ambient temperature for 40 hours. After this period, the reaction is neutralised with an aqueous bicarbonate solution, the methanol evaporated under vacuum. The mixture is extracted with dichloromethane (3 times with 5 ml), anhydrified on sodium sulphate, filtered and concentrated to residue to obtain a residue product which is purified by chromatography on silica gel (n-hexane/acetone as eluents) and thus crystallised by ethyl acetate, cyclohexane/water to obtain 78 mg of purified pimecrolimus (0.096 mmoles).

The chemical/physical characteristics of the obtained product matches the data indicated in literature for pimecrolimus.

Example 3

Screening of Lipase: Transesterification on Ascomycin and Alcoholysis on Ascomycin 33,24-diacetate (Compound V of Scheme 3)

The regioselectivity of the enzymatic reaction was determined through the use of the $^1$H-NMR analysis. The 24,33-diacetate of ascomycin (compound V) and 24- and 33-monoacetates (respectively compounds VI of scheme 3 and I of scheme 2) are not characterized in literature. The only ester of ascomycin described, is 24,33-diformiate: for this compound the protons in position 24 and 33 give two diagnostic signals respectively at 5.22 and 4.71 ppm.

Present in the spectrum of 33-monoacetate (compound I) are two peaks at 3.92 and 4.70 ppm compatible with the proposed structure.

In the spectrum of 24,33-diacetate (compound V) of ascomycin such protons fall at 5.20 and 4.70 ppm.

In the spectrum of 24-acetate (compound VI) it is observed that the region between 5.0 and 5.4 ppm is modified and peak is absent at 4.7 ppm.

Tables 1 and 2 summarise the experimental data regarding the enzymatic reactions carried out on ascomycin and ascomycin 33,24-diacetate (compound V) in esterification (transesterification), hydrolysis and alcoholysis.

TABLE 1

Enzymatic esterification of ascomycin

| Lipase | Solvent | Activated ester | Time (hours) | Conversion % (obtained products) |
|---|---|---|---|---|
| PFL | Chloroform | Vinyl acetate | 100 | 0 |
| PPL | Toluene | Vinyl acetate | 94 | 0 |
| CCL | Toluene | Vinyl acetate | 92 | 0 |
| CAL B | Acetonitrile | Vinyl acetate | 53 | 30 (33-OAc; compound I) |
| CAL B | Toluene | Vinyl acetate | 80 | 100 (33-OAc; compound I) |

PFL: lipase from *Pseudomonas cepacia* (PFL, E.C.3.1.13)
PPL: lipase from porcine pancreas (PPL; E.C.3.1.13)
CCL: lipase from *Candida cylindracea* (CCL, E.C.3.1.1.3)
CAL B: lipase from *Candida antartica* (CAL B; E.C.3.1.1.3)

TABLE 2

Alcoholysis and hydrolysis of ascomycin 33,24-diacetate (compound V of scheme 3)

| Lipase | Solvent | Solvent | Time (hours) | Conversion % (obtained products) |
|---|---|---|---|---|
| CAL B | Toluene | Water | 80 | 0 |
| CAL B | Toluene | Methanol | 48 | 0 |
| CAL B | Toluene | n-butanol | 100 | 0 |
| CAL B | Toluene | n-octan-1-ol | 120 | 30 (24-OAc; compound VI) |
| CAL B | tert-butylmethylether | n-octan-1-ol | 100 | 100 (24-OAc; compound VI) |

Example 4

Comparative

Verification of the Method of Synthesis of Pimecrolimus Described in EP427680

Imidazole (508 mg) and tert-Butyldimethylsilylchloride (1.125 g) are added in portions to a solution of 2 g (2.53 mmoles) of ascomycin in anhydrous N,N-dimethylformamide (40 ml). The reaction mixture is kept under stirring at ambient temperature for 4.5 days. The reaction is thus processed diluting it with ethyl acetate (200 ml) and processing it using water (5×100 ml). The organic phase is separated, anhydrified on sodium sulphate, filtered and evaporated to residue under vacuum to obtain a foamy raw product which is subsequently purified by chromatography on silica gel (1:30 p/p): 2.1 g (2.05 mmoles; yields 81% molars) of ascomycin 24,33 disilyl intermediate are obtained by elution with n-hexane/ethyl acetate 3/1. The chemical/physical data of such intermediate matches that indicated in EP427680.

2.1 g (2.05 mmoles) of ascomycin 24,33 disilyl intermediate are dissolved in a solution under stirring at the temperature of 0° C. composed of acetonitrile (42 ml) and aqueous HF 40% (23.1 ml). The reaction mixture is kept under stirring at the temperature of 0° C. for 2 hours then it is diluted with dichloromethane (30 ml). Then the reaction is washed in sequence with a saturated aqueous solution using sodium bicarbonate (30 ml) and water (30 m1). The separated organic phase is anhydrified on sodium sulphate, filtered and evaporated to residue under vacuum to obtain a foamy residue which is subsequently purified by chromatography on silica gel (1:30 p/p): 839 mg (0.92 mmoles; yields 45% molars) of ascomycin 24 monosilyl intermediate are obtained by elution with dichloromethane/methanol 9/1. The chemical/physical data of such intermediate matches that obtained on the compound III scheme 2 and matches the data of literature indicated in EP427680. A mixture of 839 mg (0.92 mmoles; yields 45% molars) of ascomycin 24 monosilyl intermediate, triphenylphosphine (337 mg) in carbon tetrachloride (36.4 ml) is heated under stirring under reflux for 15 hours. After this period the reaction mixture is evaporated to residue under vacuum to obtain a solid product purified by chromatography on silica gel (1:30 p/p): 535 mg (0.57 mmoles; yields 63% molars) of ascomycin 24 monosilyl intermediate, 33-chloro derivative are obtained by elution with n-hexane/ethyl acetate 2/1. The chemical/physical data of such intermediate matches those we obtained on compound IV scheme 2 and matches the data of literature indicated in EP427680.

535 mg (0.57 mmoles) of ascomycin 24 monosilyl intermediate, 33-chloro derivative are dissolved under stirring at ambient temperature in acetonitrile (16.4 ml) and aqueous HF 40% (0.44 ml). The reaction mixture is kept under stirring at ambient temperature for 45' and then it is diluted with ethyl acetate (100 ml). The organic phase is thus washed in sequence with an aqueous solution of sodium bicarbonate (70 ml) with water (2×70 ml) and thus it is anhydrified on sodium sulphate, filtered and evaporated under vacuum to obtain a solid which is subsequently purified by chromatography on silica gel (1:30 p/p): 323 mg (0.399 mmoles; yields 70% molars) of pimecrolimus is obtained by elution with n-hexane/ethyl acetate 2/3. The chemical/physical characteristics of the obtained product matches the data indicated in literature regarding pimecrolimus; the overall yield of the process is 16%.

The invention claimed is:

1. A process for preparing pimecrolimus, comprising the following steps:
   a) selective enzymatic acylation of the hydroxyl in position 33 of ascomycin with lipase from *Candida antartica*, in the presence of an acylating agent and an organic solvent;
   b) conversion of the 33-acylated derivative this obtained to the corresponding 24-tert-butyl-dimethyl-silyl ether, with a silylating agent in the presence of an organic base;
   c) enzymatic removal with lipase from *Candida antartica* of the acyl group in position 33 of the compound prepared in step b), in the presence an organic solvent and a $C_1$-$C_8$ primary aliphatic alcohol, to obtain 24-tert-butyl-dimethyl-silyl ether of ascomycin,
   wherein the hydroxyl group in position 33 of the 24-tert-butyl-dimethyl-silyl ether of ascomycin obtained in step c) is substituted with a chlorine atom to obtain a 24-tert-butyldimethylsilyl-33-epi-chloro ascomycin derivative, followed by removal of the tert-butyl-dimethyl-silyl ether in position 24.

2. The process according to claim 1, wherein the lipase from *Candida antartica* is CAL B (E.C.3.1.1.3.).

3. The process according to claim 1, wherein the acylating agent of step a) is selected from a vinyl ester and a $C_1$-$C_8$ trifluoroethyl ester.

4. The process according to claim 3, wherein the acylating agent of step a) is selected from vinyl acetate and trifluoroethyl acetate.

5. The process according to claim 1, wherein the organic solvent of steps a) and c) is an aprotic organic solvent with a coefficient of partition exceeding 0.5.

6. The process according to claim 5, wherein the organic solvent of step a) is toluene, n-hexane, n-heptane, dichloromethane, chloroform or tert-butyldimethylether and the organic solvent of step c) is tert-butyldimethylether, dichloromethane or toluene.

7. The process according to claim 6 wherein the organic solvent of step c) is tert-butyldimethylether.

8. The process according to claim 1, wherein the silylating agent of step b) is tert-butyldimethylsilyl chloride or tert-butyldimethylsilyl triflate.

9. The process according to claim 1, wherein the organic base of step b) is imidazole, pyridine or 2,6-lutidine.

10. The process according to claim 9, wherein the organic base of step b) is 2,6-lutidine.

11. The process according to claim 1, wherein the primary aliphatic alcohol of step c) is n-octan-1-ol.

12. The process according to claim 1, wherein the substitution of the hydroxyl group in position 33 of 24-tert-butyl-dimethyl-silyl ether of ascomycin with a chlorine atom is carried out using dichlorotriphenylphosphorane or N-chlorosuccinimide.

13. The process according to claim 1, wherein the removal of the tert-butyl-dimethyl-silyl ether in position 24 is carried out by means of acid catalysis with monoprotic inorganic acids or organic acids.

14. The process according to claim 13, wherein the removal of the tert-butyl-dimethyl-silyl ether in position 24 is carried out by means of acid catalysis with fluorhydric acid, hydrochloric acid, p-toluenesulfonic acid monohydrate or methanesulfonic acid.

15. The process according to claim 14, wherein the removal of the tert-butyl-dimethyl-silyl ether in position 24 is carried out by means of acid catalysis with p-toluenesulfonic acid monohydrate.

16. The process according to claim 1, wherein step a) comprises:
preparing acetylated aseomycin in positions 24 and 33, starting from ascomycin and an acylating agent in an organic solvent, in the presence of N,N-dimethylaminopyridine, and step b) comprises:
enzymatic removal with lipase from Candida antartica of the acyl in position 33 of the compound prepared in step a'), in the presence of an organic solvent and a $C_1$-$C_8$ primary aliphatic alcohol, obtaining monoacetylated ascomycin at position 24.

17. The process according to claim 16, wherein the acylating agent of step a) is acetyl chloride or acetic anhydride.

18. The process according to claim 16, wherein the organic solvent of step a) is an organic base.

19. The process according to claim 18, wherein the organic base is pyridine or triethylamine.

20. The process according to claim 16, wherein the organic solvent of step b) is an aprotic organic solvent with a coefficient of partition exceeding 0.5.

21. The process according to claim 16, wherein the organic solvent of step b) is tert-butyldimethylether, dichloromethane or toluene.

22. The process according to claim 21, wherein the organic solvent of step b) is tert-butyldimethylether.

23. The process according to claim 16, wherein the primary aliphatic alcohol of step b) is n-octan-1-ol.

24. The process according to claim 16, comprising substitution of the hydroxyl group in position 33 of the monoacetylated ascomyein at position 24 with a chlorine atom to obtain 24-acetate-33-epi-chloro aseomycin derivative, and subsequent removal of the acetate in position 24.

25. The process according to claim 24, wherein the substitution of the hydroxyl group in position 33 of the monoacetylated ascomycin at position 24 with a chlorine atom is carried out using polymer-supported triphenylphosphine, in a $C_1$-$C_2$ chlorinated solvent in the presence of another nonpolar aprotic organic solvent.

26. The process according to claim 25, wherein the $C_1$-$C_2$ chlorinated solvent is carbon tetrachloride or hexachloroethane.

27. The process according to claim 25, wherein the nonpolar aprotic organic solvent is a linear or branched $C_5$-$C_8$ aliphatic hydrocarbon or an aromatic hydrocarbon.

28. The process according to claim 27, wherein the nonpolar aprotic organic solvent is toluene or xylene.

29. The process according to claim 24, wherein the removal of the acetate in position 24 is carried out by means of acid catalysis with monoprotic inorganic acids or organic acids.

30. The process according to claim 29, wherein the removal of the acetate in position 24 is carried out by means of acid catalysis with fluorhydric acid, hydrochloric acid, p-toluenesulfonic acid monohydrate or methanesulfonic acid.

31. The process according to claim 30, wherein the removal of the acetate in position 24 is carried out by means of acid catalysis with hydrochloric acid.

32. 24,33-diacetate ascomycin of formula:

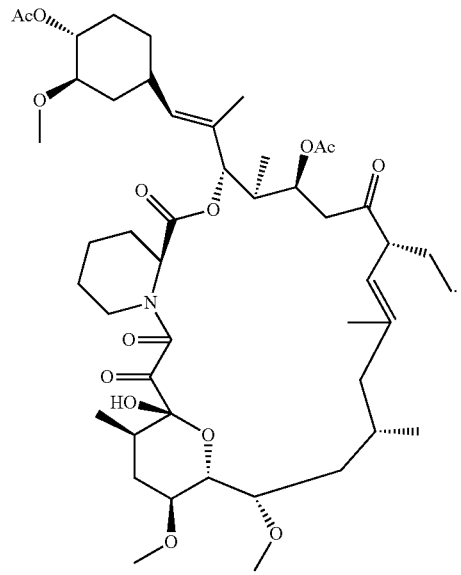

Compound V 33. 24-monoacetate ascomycin of formula:

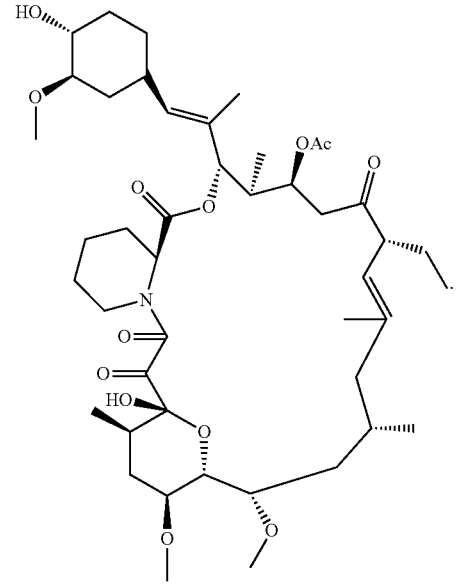

Compound VI

34. 24-acetate-33-epi-chloro ascomycin of formula:
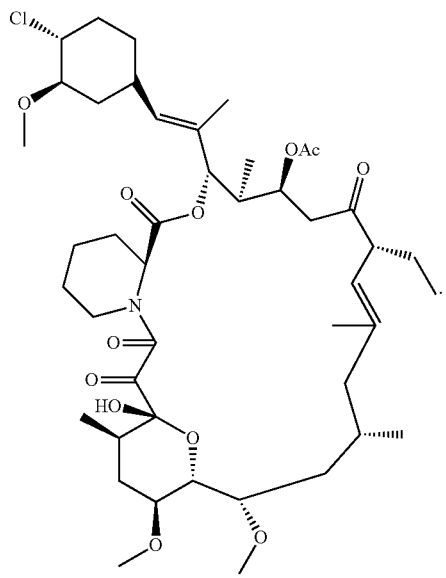
Compound VII
35. 24-tert-butyldimethylsilyl-33-acetyl-ascomycin of formula:
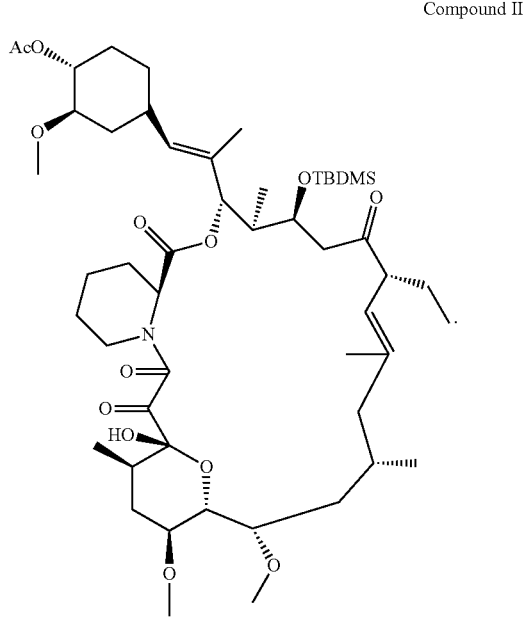
Compound II
* * * * *

UNITED STATES PATENT AND TRADEMARK OFFICE
CERTIFICATE OF CORRECTION

PATENT NO. : 8,778,636 B2  
APPLICATION NO. : 13/261036  
DATED : July 15, 2014  
INVENTOR(S) : Grisenti et al.

Page 1 of 1

It is certified that error appears in the above-identified patent and that said Letters Patent is hereby corrected as shown below:

On the Title Page, Item [56] Other Publications, International Search Report:
Delete "PCT/1132010/052218" and insert --PCT/IB2010/052218--.

On the Title Page, Item [56] Other Publications, IPRP:
Delete "PCT/1132010/052218" and insert --PCT/IB2010/052218--.

On the Title Page, Item [56] Other Publications, Wang, et al.:
Delete "1988, 3127-3129" and insert --1988, 53, 3127-3129--.

In the Claims

Column 25, Claim 34, Line 5 - 30, Formula: Delete

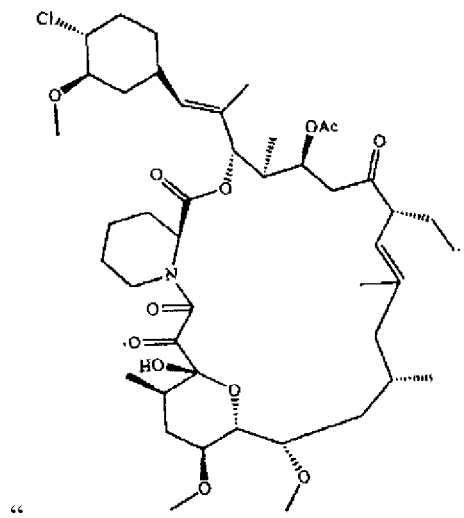

" and insert --

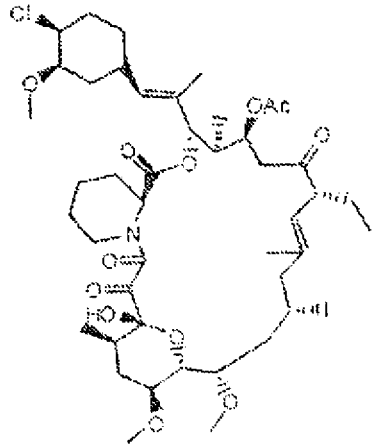

--.

Signed and Sealed this  
Fourth Day of November, 2014

Michelle K. Lee  
*Deputy Director of the United States Patent and Trademark Office*